(12) United States Patent
Lauritsch et al.

(10) Patent No.: US 7,359,477 B2
(45) Date of Patent: Apr. 15, 2008

(54) METHOD FOR RECONSTRUCTING A CT IMAGE USING AN ALGORITHM FOR A SHORT-SCAN CIRCLE COMBINED WITH VARIOUS LINES

(75) Inventors: Günter Lauritsch, Erlangen (DE); Frank Dennerlein, Eckental (DE)

(73) Assignee: Siemens Aktiengesellschaft, Munich (DE)

( * ) Notice: Subject to any disclaimer, the term of this patent is extended or adjusted under 35 U.S.C. 154(b) by 218 days.

(21) Appl. No.: 11/057,978

(22) Filed: Feb. 15, 2005

(65) Prior Publication Data

US 2006/0182216 A1  Aug. 17, 2006

(51) Int. Cl.
*A61B 6/03* (2006.01)
(52) U.S. Cl. .............. 378/4; 378/210; 378/901
(58) Field of Classification Search ............ 378/4, 378/205, 210, 901; 382/131
See application file for complete search history.

(56) References Cited

U.S. PATENT DOCUMENTS

| 5,442,674 | A  | * | 8/1995 | Picard et al. ............... 378/20 |
| 6,049,582 | A  | * | 4/2000 | Navab ........................ 378/4 |
| 6,379,041 | B1 | * | 4/2002 | Schuetz et al. ............ 378/205 |
| 2005/0129168 | A1 | * | 6/2005 | Morita ........................ 378/4 |
| 2006/0034417 | A1 | * | 2/2006 | Katsevich .................. 378/4 |

OTHER PUBLICATIONS

Katsevich, Image reconstruction for the circle and line trajectory, Oct. 25, 2004, Phys. Med. Biol., 49, p. 5059-5072.*
Shakarji, Least-Squares Fitting Algorithm of the NIST Algorithm Testing System, Journal of Research of the National Institute of Standards and Technology, Nov.-Dec. 1998, vol. 103, No. 6, pp. 633-641.*
Jiang et al., Fitting 3D circles and Ellipses using a parameter decomposition approach, Proceedings of the Fifth International Conference on 3-D Digital Imaging and Modeling, 2005, Jun. 13-16, 2005, pp. 103-109.*
Mitschke et al., Recovering the X-ray projection geometry for three-dimensional tomographic reconstruction with additional sensors: Attached camera versus external navigation system, 2003, Medical Image Analysis, 7, pp. 65-78.*
Richard Hartley, Andrew Zisserman "Multiple View Geometry in Computer Vision algorithms for cone beam CT" Cambridge University Press, Jun. 200, pp. 138-165.
Katsevich Alexander "A General Scheme For Constructing Inversion Algorithms For Cone Beam CT" International Journal of Mathematics and Mathematical Sciences, vol. 2003 (2003), Issue 21, pp. 1305-1321.

(Continued)

*Primary Examiner*—Edward J. Glick
*Assistant Examiner*—John M Corbett
(74) *Attorney, Agent, or Firm*—Schiff Hardin LLP

(57) ABSTRACT

In a method for reconstructing a CT image from data acquired from an examination subject, a reconstruction algorithm is employed that is based on an ideal short-scan circle-and-line trajectory. To adapt the reconstruction algorithm to a "real world" scan trajectory, data are acquired with a C-arm CT apparatus wherein the focus is moved through an actual short-scan circle-and-line trajectory. For each position of the focus in the actual trajectory, a projection matrix is electronically generated and the reconstruction algorithm with the ideal trajectory is adapted to the actual trajectory using the projection matrices.

7 Claims, 2 Drawing Sheets

OTHER PUBLICATIONS

Grass et al. "Three-dimensional reconstruction of high contrast objects using C-arm image intensifier projection data" Comp. Med. Imag. and Graphics 23, pp. 311-321, (1999).

Zellerhoff et al. "Low contrast 3D-reconstruction from C-arm data" Proceedings of SPIE, Medical Imaging 2005, vol. 5745, pp. 646-655.

Kudo et al. Fast and stable cone-beam filtered backprojection method for non-planar orbits Phys. Med. Biol. 43 747-760, Print publication: Issue 4 (Apr. 1996).

Pack et al. "Investigation of saddle trajectories for cardiac CT imaging in cone-beam geometry" Phys Med. Biol. 49 2317-2336, Print publication: Issue 11 (Jun. 7, 2004).

Wiegert et al. "Soft tissue contrast resolution within the head of human cadaver by means of flat detector based cone-beam CT" Medical Imaging 2004: Physics of Medical Imaging. Edited by Yaffe, Martin J.; Flynn Michael J.; Proceedings of the SPIE, vol. 5368, pp. 330-337, 2004.

Heang K. Tuy "An Inversion Formula For Cone-Beam Reconstruction" SIAP vol. 43, Issue 3, pp. 546-552, © Society for Industrial and Applied Mathematics.

Hermann Schomberg "Complete Source Trajectories for C-Arm Systems and a Method for Coping with Truncated Cone-Beam Projections", Biomedical Imaging: Macro to Nano, 2004. IEEE International Symposium on Apr. 15-18, 2004, pp. 575-578, vol. 1.

Ning et al. "Flat panel detector-based cone beam computed tomography with a circle-plus-two-arcs data acquisition orbit:: Preliminary phantom study", Medical Physics, Jul. 2003, vol. 30, Issue 7, pp. 1694-1705.

Zeng et al. "A cone-beam tomography algorithm for orthogonal circle-and-line orbit" Phys. Med. Biol., vol. 37, No. 3 Mar. 1992, pp. 563-577.

Johnson et al. "Feldkamp and circle-and-line cone-beam reconstruction for 3D micro-CT of vascular networks" Physics in Medicine and Biology, vol. 43, Issue 4, pp. 929-940 (1998).

Dennerlein et al. "Exact and efficient cone-beam reconstruction algorithm for a short-scan circle combined with various lines" Proceedings of SPIE, vol. 5747, Medical Imaging 2005:.

Frank Dennerlein "3D Image Reconstruction from Cone-Beam Projections using a Trajectory consisting of a Partial Circle and Line Segments" Master Thesis in Computer Science, Patter Recognition Chair, FAU, 2004.

* cited by examiner

METHOD FOR RECONSTRUCTING A CT IMAGE USING AN ALGORITHM FOR A SHORT-SCAN CIRCLE COMBINED WITH VARIOUS LINES

BACKGROUND OF THE INVENTION

1. Field of the Invention

The present invention is directed to a method for reconstructing a CT image, and in particular to reconstructing a CT image using a reconstruction algorithm for a short-scan circle combined with various lines.

2. Description of the Prior Art

Tomographic imaging of high contrast objects based on cone-beam projections acquired on C-arm systems as described, for example, in M. Grass, R. Koppe, E. Klotz, R. Proksa, M. Kuhn, H. Aerts, J. O. de Beck, and R. Kempkers, "Three-dimensional reconstruction of high-contrast objects using C-arm image intensifier projection data," *Comp. Med. Imag. and Graphics* 23, pp. 311-321, 1999 has become established in a clinical, interventional environment. In particular in neuroradiology the 3D representation of the complex vascular tree is of high clinical value to plan or validate therapy. Due to the invasive, arterial injection of contrast agent the vascular tree possesses a much higher contrast to the surrounding tissue such as e.g. bone. Thus, the procedure is relatively insensitive to distortions and image artifacts. Recent improvements in data acquisition, e.g. by use of flat panel detectors, will shift clinical applications towards imaging of low-contrast objects. For example, diagnosis and treatment of stroke on the same C-arm device is a highly desirable goal. This would require that hemorrhage in brain matter be ruled out before treating ischemia. According to current clinical protocols this is done by a native computed tomography (CT) scan. Soft tissue imaging requires accurate data acquisition and processing as described in M. Zellerhoff, B. Scholz, E.-P. Ruehrnschopf, and T. Brunner, "Low contrast 3D-reconstruction from C-arm data," in *Proc. SPIE* 5745, to be published, 2005 and J. Wiegert, M. Bertram, D. Schaefer, N. Conrads, N. Noordhoek, K. de Jong, T. Aach, and G. Rose, "Soft tissue contrast resolution within the head of human cadaver by means of flat detector based cone-beam CT," in *Proc. SPIE* 5368, pp. 330-337, 2004. A serious limitation is the incompleteness of projection data acquired by a conventional short-scan circular source trajectory. Cone artifacts, which result from that incompleteness, occur as a smearing and shading artifact and may superpose severely important low contrast details.

Numerous investigations on source trajectories that satisfy Tuy's completeness condition (see H. K. Tuy, "An inversion formula for cone-beam reconstruction," in *SIAM J. Appl. Math,* 1983) can be found in the literature: saddle trajectory (J. Pack, F. Noo, and H. Kudo, "Investigation of saddle trajectories for cardiac CT imaging in cone-beam geometry," *Phys. Med. Biol.* 49, pp. 2317-2336, 2004) selection of non-planar, non-closed trajectories optimized for C-arm devices, (H. Schomberg, "Complete source trajectories for C-arm systems and a method for coping with truncated cone-beam projections," in *Proc. Meeting on Fully 3-D Image Reconstruction in Radiology and Nucl. Med.,* 2001) circle and arc trajectory optimized for CT gantries, (R. Ning, X. Tang, D. Conover, and R. Yu, "Flat panel detector-based cone beam computed tomography with a circle-plus-two-arcs data acquisition orbit: Preliminary phantom study," *Med. Phys.* 30, pp. 1694-1705, 2003) circle and line trajectory (G. L. Zeng and G. T. Gullberg, "A cone-beam tomography algorithm for orthogonal circle-and-line orbit," *Phys. Med. Biol.* 37, pp. 563-577, 1992, and R. Johnson, H. Hu, S. Haworth, P. Cho, C. Dawson, and J. Linehan, "Feldkamp and circle-and-line cone-beam reconstruction for 3D micro-CT of vascular networks," *Phys. Med. Biol.* 43, pp. 929-940, 1998 and H. Kudo and T. Saito, "Fast and stable cone-beam filtered back-projection method for non-planar orbits," *Phys. Med. Biol.* 43, pp. 747-760, 1998) and many others.

SUMMARY OF THE INVENTION

It is an object of the present invention to provide a method for reconstructing a CT image employing an algorithm using a short-scan circle and line trajectory that can be easily realized on existing C-arm device without any hardware modifications. The line scan can be regarded as an add-on to the conventional short-scan circular path. The approach should be theoretically exact, possess efficient, shift-invariant filtered back-projection (FBP) structure, and solve the long object problem. The algorithm should be flexible in dealing with various circle and line configurations. The reconstruction method should require nothing more than the theoretically minimum length of scan trajectory.

These objects are achieved in accordance with the present invention in a method for reconstructing a CT image of a subject from data acquired from the subject with a C-arm apparatus, having an x-ray source with a focus from which x-rays emanate in a cone beam, and a radiation detector, mounted on a C-arm, by rotating the focus of the x-ray source around the subject through a focus trajectory and detecting radiation attenuated by the subject with the radiation detector. In accordance with the invention, the C-arm is operated to move the focus of the x-ray source through an actual focus trajectory consisting of an actual incomplete circle and an actual straight-line segment attached at an end of the actual incomplete circle, and detecting radiation attenuated by the subject for each focus position in the actual focus trajectory. For each position of the focus in the actual focus trajectory, a projection matrix is electronically calculated that, for that focus position, describes a perspective cone beam projection of the subject on the radiation detector. An image of the subject is reconstructed using a known reconstruction algorithm that is based on an ideal focus trajectory consisting of an ideal incomplete circle and an ideal straight-line segment attached at an end of the ideal incomplete circle, with the ideal trajectory in the known reconstruction algorithm being adapted to the actual trajectory of the C-arm apparatus using the projection matrices.

The inventive reconstruction algorithm is based on a reconstruction algorithm that uses an ideal source trajectory known from A. Katsevich, "Image reconstruction for the circle and line trajectory," *Phys. Med. Biol.* 49, pp. 5059-5072, 2004 (from which the discussion below regarding the known inversion algorithm, and FIGS. 1-4, are taken) and A. Katsevich, "A general scheme for constructing inversion algorithms for cone beam CT," *International Journal of Mathematics and Mathematical Sciences* 21, pp. 1305-1321, 2003. However, C-arm devices exhibit certain mechanical instabilities that have to be considered. Fortunately, the geometrical deviations from the ideal source path are almost reproducible and are accounted for by a geometrical calibration process. The projection geometry of non-ideal source trajectories is described conveniently in the framework of projection matrices. The general use of projection matrices for describing projection geometry is discussed in R. Hartley and A. Zisserman, *Multiple View Geometry in Computer Vision*, Cambridge University Press, 2000. The back-projection step is performed exactly by a direct use of projection matrices. The filtering step requires a more elaborate adaption strategy. The inventive method is a simple but robust scheme to adapt the reconstruction algorithm to non-ideal sampling patterns as they occur in imaging with real world C-arm devices.

DESCRIPTION OF THE PREFERRED EMBODIMENTS

In the discussion below, the known inversion algorithm for an ideal short-scan (incomplete) circle-and-line trajectory is discussed. This is followed by a discussion of the adaptation of the algorithm to source paths that deviate from the ideal trajectory, in accordance with the inventive method. Lastly, there follows a discussion of experiments demonstrating the applicability of the inventive reconstruction algorithm.

Known Inversion Algorithm for an Ideal Short-Scan Circle- and Line Trajectory

Figure 1:
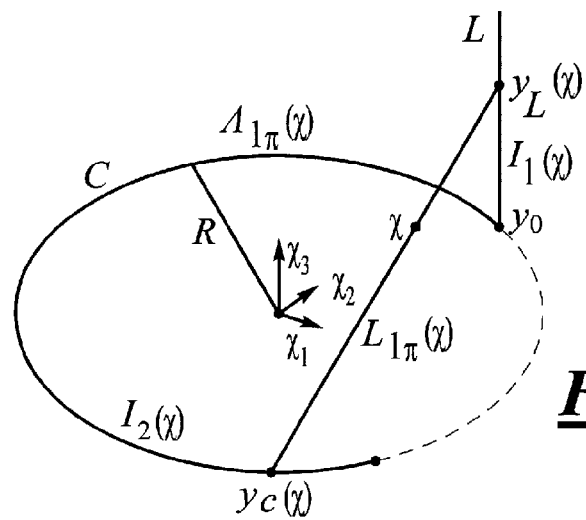
FIG. 1 illustrates the basic circle and line trajectory for use in explaining the inventive method.

Consider the source trajectory consisting of an incomplete circle C and a line segment L attached to C at one of the endpoints of C (see FIG. 1). At first we assumed that C is sufficiently close to a complete circle, and L is sufficiently long. Let $y_o$ be the point where they intersect. It is assumed that the detector array DP(s) is flat, contains the $x_3$-axis (the axis of C), and is perpendicular to the shortest line segment connecting the source y(s) and the $x_3$-axis.

FIG. 1 illustrates the circle and line trajectory.

The following notations are used. S2 is the unit sphere in IR3, and $$Df(y, \Theta) := \int_0^\infty f(y + \Theta t)\, dt, \Theta \in S^2; \quad (1)$$

$$\beta(s, \chi) := \frac{x - y(s)}{|x - y(s)|};$$

$$\Pi(x, \xi) := \{z \in IR^3 : (z - x) \cdot \xi = 0\}.$$

It is assumed that f is smooth, compactly supported, and identically equals zero in a neighborhood of the source trajectory.

Suppose $I_1 \ni s \to y(s) \in L$ and $I_2 \ni s \to y(s) \in C$ are parameterizations of the line and circle, respectively. It is assumed that the circle is of radius R and centered at the origin. Let U be an open set, such that $U \subset \{(x_1, x_2, x_3) \in IR^3 : x_1^2 + x_2^2 < R^2\}$.

Pick a reconstruction point $x \in U$, and consider the plane $\Pi(x)$ through x and L. $\Pi(x)$ intersects C at two points. One of them is $y_o$, and the second is denoted $y_C(x)$. Let $L_{1\pi}(x)$ be the line segment containing x and connecting $y_C(x)$ to L (see FIG. 1). Then $Y_L(x) \in L$ denotes the other endpoint of $L_{1\pi}(x)$ The known procedure determines two parametric intervals.

The first one $I_1(x) \subset I_1$ corresponds to the section of L between $y_o$ and $Y_L(x)$. The second one $I_2(x) \subset I_2$ corresponds to the section of C between $y_o$ and $Y_C(x)$. The section of $C \cup L$ bounded by $L_{1\pi}(x)$ is denoted $\Lambda_{1\Pi}(x)$. It is easily seen that $\Lambda_{1\Pi}(x)$ is complete in the sense of Tuy.

Consider intersections of planes through x with $\Lambda_{1\Pi}(x)$. Neglecting planes tangent to the trajectory, there can be either one or three intersection points (IPs). Moreover, there can be at most one IP belonging to L. In view of this argument, the data in Table 1 defines the weight function n up to a set of measure zero.

The role of n is twofold. First, it has to deal with redundancy in the cone beam data by assigning weights to IPs between Radon planes and the source trajectory. Second, a proper choice of n yields an efficient shift-invariant convolution back-projection algorithm in the framework of Katsevich's general inversion formula. The function n, described by Table 1, can be described as follows. If there is one IP, it is given weight 1. If there are three IPs, the two IPs on the circle have weight 1 each, and the IP on the line segment has weight −1. As is easily seen, n is normalized:

$$\sum_j n(s_j, x, \alpha) = 1$$

for almost all $\alpha \in S^2$. Here the summation is over all intersection points $y(s_j) \in \Pi(x, \alpha) \cap \Lambda_{1\pi}(x)$.

TABLE 1

| Definition of the weight function n(s, x, α) | |
|---|---|
| Case | n |
| 1IP, $s_1 \in I_1(x)$ | $n(s_1, x, \alpha) = 1$ |
| 1IP, $s_1 \in I_2(x)$ | $n(s_1, x, \alpha) = 1$ |
| 3IPs, $s_1 \in I_1(x)$ | $n(s_1, x, \alpha) = -1$ |
| $s_2, s_3 \in I_2(x)$ | $n(s_k, x, \alpha) = 1, k = 2, 3$ |

Denote $$\phi(s, x, \theta) := \text{sgn}(\alpha \cdot \dot{y}(s)) n(s, x, \alpha), \alpha = \alpha(\theta) \in \beta^\perp(s, x), \quad (2)$$

where θ is a polar angle in the plane perpendicular to β(s,x). According to the general scheme, described by Katsevich, jumps of φ(s,x,θ) have to be located in θ. By studying these jumps in two cases: $s \in I_1(x)$ and $s \in I_2(x)$ and using the general scheme the following inversion algorithm is obtained. Pick $s \in I_1(x)$ (i.e., y(s) is on the line). Find a plane through x and y(s), which is tangent to C at some $y_t(s,x)$, $s \in I_2(x)$. Let $u_1(s,x)$ be the unit vector perpendicular to that plane:

$$u_1(s, x) := \frac{(y_t(s, x) - y(s)) \times \beta(s, x)}{|(y_t(s, x) - y(s)) \times \beta(s, x)|}, x \in U, s \in I_1(x). \quad (3)$$

Pick now $s \in I_2(x)$ (i.e., y(s) is on the circle) and define $$u_2(s, x) := \frac{\dot{y}(s) \times \beta(s, x)}{|\dot{y}(s) \times \beta(s, x)|}, x \in U, s \in I_2(x). \quad (4)$$

By construction, $u_2(s,x)$ is the unit vector perpendicular to the plane containing x, y(s), and tangent to C at y(s). Using (3) and (4) we obtain the following reconstruction formula for $f \in C_0^\infty(U)$:

$$f(x) = \qquad (5)$$

$$-\frac{1}{2\pi^2} \sum_{k=1}^{2} \int_{I_k(x)} \frac{\delta_k(s,x)}{|x-y(s)|} \int_0^{2\pi} \frac{\partial}{\partial q} D_f(y(q), \Theta_k(s,x,\gamma))\Big|_{q=s} \frac{d\gamma}{\sin\gamma} ds,$$

where $$\Theta_k(s,x,\gamma) := \cos\gamma \beta(s,x) + \sin\gamma e_k(s,x), e_k(s,x) := \beta(s,x) \times u_k(s,x). \qquad (6)$$

and $\delta_k$ is defined as follows:

$$\delta_1(s,x) = -sgn(u_1(s,x)\cdot\dot{y}(s)), s \in I_1(x); \delta_2(s,x) = 1, s \in I_2(x). \qquad (7)$$

Suppose, for example, that L is parameterized in such a way that the source moves down along L as s increases. Then $\delta_1(s, x)=1, s \in I_1(x)$. If the source moves up along L as s increases, then $\delta_1(s, x)=1, s \in I_1(x)$.

Figure 2:
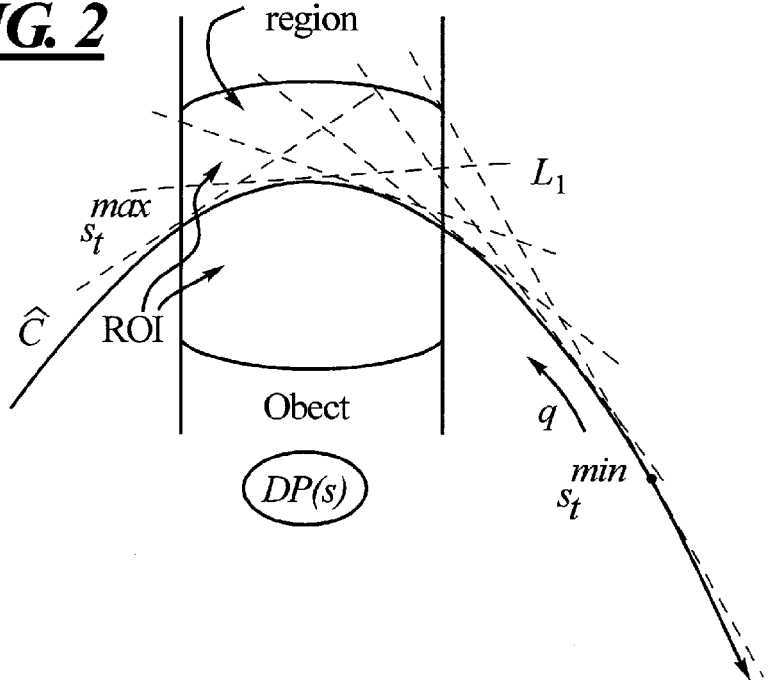
FIG. 2 illustrates the projection onto the detector plane when the source is on the line.

FIG. 2 illustrates the projection onto the detector plane when the source is on the line.

Consider now the computational structure of the algorithm. Pick $y(s) \in L$. For a point $x \in U$ we have to find $s_t \in I_2(x)$. This determines the filtering line on the detector, which is tangent to $\hat{C}$ at $\hat{y}(s_t)$. Here $\hat{C}$ and $\hat{y}(s_t)$ are projections onto the detector plane of C and $y(s_t)$, respectively. It is easy to see that all other $x \in U$ which project onto this line to the left of $y(s_t)$ will share it as their filtering line. Hence, we can first perform filtering along lines on the detector tangent to $\hat{C}$ (see family $L_1$ in FIG. 2), and then perform back-projection. The range of $s_t$ values, $$\smin_t \leq s_t \leq \smax_t,$$

depends on the region of interest (ROI) and is illustrated in FIG. 2. It is easily seen that filtering is shift-invariant, and consists of convolving $$\frac{\partial}{\partial q} D_f(y(q), \Theta_k(s, \cdot, \gamma))\Big|_{q=s}$$

with $1/\sin\gamma$.

Figure 3:
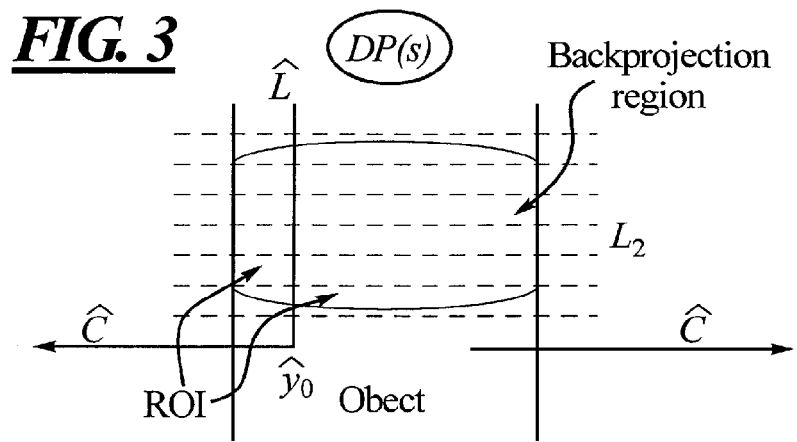
FIG. 3 illustrates the projection onto the detector plane when the source is on the circle.

FIG. 3 illustrates the projection onto the detector plane when the source is on the circle.

If $y(s) \in C$, filtering must be performed along lines on the detector parallel to $\dot{y}(s)$. The resulting family is denoted $L_2$ in FIG. 3. Pick any line from $L_2$. One shows that all x whose projection belongs to that line and appears to the right of $\hat{L}$ share it as their filtering line. As before, one can first perform filtering (i.e., convolution with $1/\sin\gamma$) along these lines, and follow it by back-projection. Hence the resulting algorithm is of the convolution-based FBP type.

Some properties of this algorithm are as follows. From the construction of $L_{1\pi}(x)$, $_{yL}(x) \to y_0$ as $x_3 \to 0$. In the limit $x_3=0$, $y_L(x)=y_0$, so the integral over L in (5) disappears, and the integral over C becomes a very short scan fan-beam reconstruction formula.

Given specific C and L, the part of the support of f that can be accurately reconstructed by the algorithm can be determined. This is the volume bounded by the following three surfaces: the plane of C, the plane defined by L and the endpoint of C not on L, and the conical surface of lines joining the points of C to the endpoint of L that is not on C. This volume will be denoted U(C, L). It should be noted, however, that the object f may extend outside U(C, L), as long as it stays away from the source trajectory C∪L.

Figure 4A:
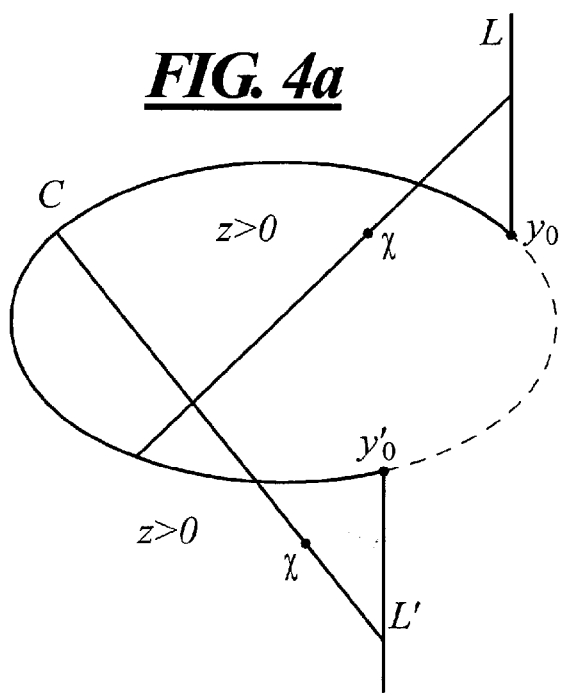
FIGS. 4*a* and 4*b* respectively illustrate examples of trajectories that can be handled using the inventive method.
Figure 4B:
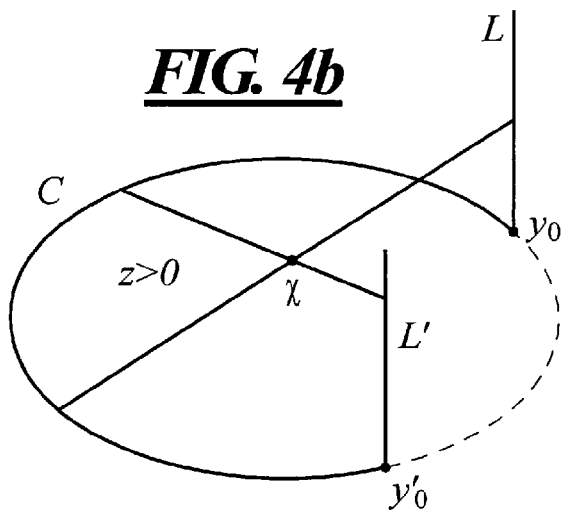

The trajectory consisting of an incomplete circle and a line segment can be used as a building block for constructing other trajectories. For example, one can consider an incomplete circle C with line segments attached to it at each endpoint of C. These segments can be on opposite sides of C (see FIG. 4), or on the same side of C (see FIG. 4b). Inversion algorithms for these trajectories are obtained from (5) by applying it to each circle+line subset and then adding the results (if necessary). Indeed, suppose the segments are on opposite sides of C. Then the volume U(C, L) in the half-space $z \geq 0$ is reconstructed using the trajectory C∪L, and the volume U(C, L') in $z \leq 0$ is reconstructed using C∪L'. In this case no summation is needed. If L and L' are on the same side of C, then reconstruction is done only in the half-space $z \geq 0$. In this case each voxel in the volume U(C, L)∩U(C, L') is reconstructed twice: using C∪L and C∪L', so the summation is used. This does not mean that reconstruction time is twice as long. First, the line portions of the scan L and L' are used only one time each. Second, only a part of the circle C is used twice. This does not lead to any increase in computational time, because filtering and back-projection are identical in both cases. Consequently, a simple post-filtering weight solves the problem of multiple contributions to any given voxel.

Consider now the overall detector requirements. It is assumed that L and L' are on the opposite sides of C, and the reconstruction volume is $$\{(x_1, x_2, x_3) : x_1^2 + x_2^2 \leq r^2, -H \leq x_3 \leq H\}.$$

The circular scan thus requires a rectangular detector of a size $$|d_1| \leq \frac{r}{\sqrt{1-(r/R)^2}}, |d_2| \leq \frac{H}{1-(r/R)}. \qquad (8)$$

Here $d_1$ and $d_2$ are the horizontal and vertical axes on the detector. Katsevich has shown that the line scans require the detector of size $$|d_1| \leq \frac{r}{\sqrt{1-(r/R)}}, |d_2| \leq \frac{H}{1-(r/R)} \frac{1}{1-(r/R)^2}. \qquad (9)$$

Hence the addition of line scans increases the detector height compared with the conventional Feldkamp-type circular reconstruction only by a factor $1/(1-(r/R)^2)$.

Adaptation of the Known Algorithm to Non-Ideal Source Trajectories

The exact, known reconstruction algorithm described above presumes an ideal acquisition geometry. Data acquisition with a C-arm device, however, never fulfills these ideal geometry presumptions. The movements of the acquisition system are influenced by mechanical phenomena, such as gravity and inertia, leading to different non-ideal types of focus trajectories—a phenomena that has to be considered in the reconstruction approach.

The non-ideal acquisition geometry of a real world C arm device is represented in the inventive method by a sequence of homogenous projection matrices $P_s \in \mathbb{R}^{3 \times 4}$. For every source position s, and thus for every measured projection image, the matrix $P_s$ completely describes the perspective cone beam projection of the object. More precisely, the matrix defines the relation between every voxel $x_h$ of the object and the coordinates wh of the corresponding detector image point $$w_h = P_s x_h, \quad (10)$$

where a voxel with a Cartesian coordinate vector x is denoted by the homogenous vector $x_h = (b \cdot x^T, b)$ with $b \in \mathbb{R} \backslash 0$ and an analog notation for a Cartesian detector position $w = (u^{pix}, v_{pix})^T$ is $w_h = (c \cdot w_T, c)^T, c \in \mathbb{R} \backslash 0$. $u_{pix}$ and are the coordinate values of an image point measured along the two perpendicular axes' vectors $e_{u,s}$ respectively $e_{v,s}$ that coincide with the row or the column direction of the pixel grid of the detector DP(s).

As the deviations in acquisition geometry vary from C-arm device to C-arm device, but remain almost constant for successive scans on the same device, an essential task is to determine an individual, valid sequence of $P_s$ for a given C-arm system. This geometric calibration is done by an automated procedure involving a calibration phantom of exactly defined structure and an appropriate calibration algorithm that calculates a valid matrix $P_s$ for a given s.

A matrix $P_s$ can be decomposed in a complete set of projection parameters. Especially the extrinsic parameters are of interest as they include position and orientation of the involved detector and focus entities. The inventive method calculates the focus positions and the direction vectors of the pixel coordinate system's axes from every $P_s$. By that the acquisition trajectory can be composed and when using matrices downloaded from a real world C-arm device, it is possible to determine the deviations of the acquisition geometry compared to the ideal circle and line geometry presumed by the reconstruction approach. For convenience the matrices $M_s \in \mathbb{R}^{3 \times 3}$ are introduced, consisting of the first three columns of the $P_s$. Note that all $M_s$ are invertible.

The focus position y(s) is calculated as $$y(s) = M_s^{-1} P_s (0,0,0,1)^T. \quad (11)$$

The projection matrices define the detector only up to scale. To have knowledge about the precise structure of the C-arm acquisition system, either the specification of the focus-detector distance or the detector pixel spacing is needed. The direction of the two axis of the detector pixel coordinate system, however, is universally valid. $e_{u,s}$ is parallel to the vector $((0,0,1) \cdot Ms)^T \times ((1,0,0) \cdot M_s)^T$ and $e_{v,s}$ points in the direction $((0,0,1) \cdot Ms)^T \times ((0,1,0) \cdot M_s)^T$. Further, the detector coordinates $w_{0,s}$ of the intersection of the optical axis and the detector plane are calculated as $w_{0,s} = M_s \cdot (0,0,1) M_s$. It turns out that the real path can vary up to 2% in radial direction from an ideal circle. Further, the focus positions are not located within a plane, but vary in longitudinal direction. A relative movement of focus and detector appears when the C-arm is in motion. Tilt and rotational deviations are not very prominent, but the translational in-plane movement of the detector during the acquisition run is considerable. The known reconstruction algorithm derived for an ideal circle and line trajectory has to be adapted to the non-ideal source paths of real C-arm devices.

In accordance with the invention for an application of the circle and line reconstruction approach the following general strategy is applied. The projection matrix $P_s$ exactly describes the relation between the object and its cone beam projection image for every s. By that, an exact consideration of the non-ideal acquisition geometry in the back-projection step is possible by the direct use of the projection matrices. For the filtering step the case of non-ideal trajectory is transferred into the ideal case approximately. The presumed ideal trajectory consisting of a partial circle and a perpendicularly attached line segment is fitted into the set of real world focus positions. The fitted circle path again projects as a parabola onto the detector and the same approach as described above can be used to determine the filtering directions as tangents to the occurring parabola.

Figure 5:
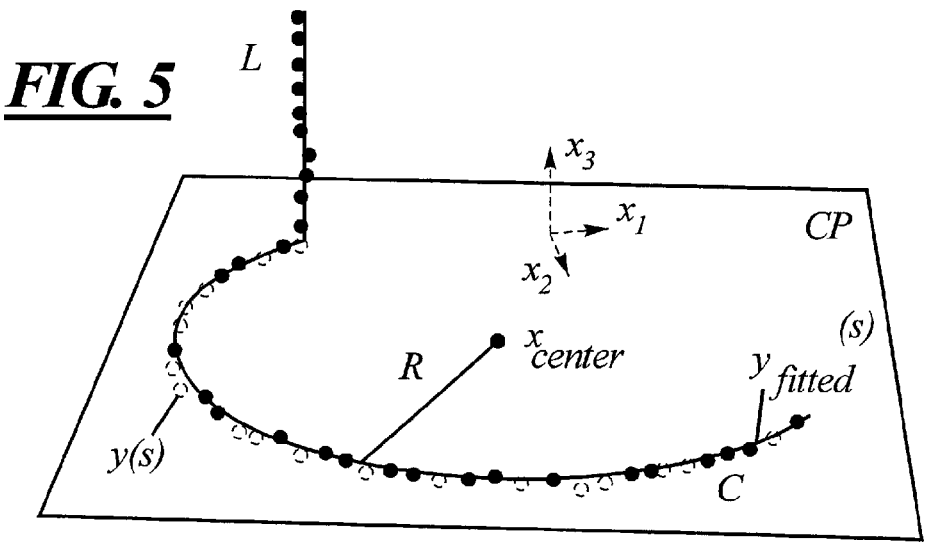
FIG. 5 illustrates the fit of an ideal circle and line trajectory into the set of real world (actual) focus positions, in accordance with the inventive method.

FIG. 5 illustrates the fit of an ideal circle and line trajectory $y_{fitted}(s)$ into the set of real world focus positions y(s). A dotted source position is located below the circular plane CP.

Any appropriate cost function can be used to fit the ideal trajectory $y_{fitted}(s)$ into the path y(s). In the following a least-square fit is described. The least-square fit of the ideal trajectory $y_{fitted}(S)$ into the path y(s), as illustrated in FIG. 5 corresponds to the minimization of the total estimation error $$\epsilon = \sum_s (\|y_{fitted}(s) - y(s)\|^2) \quad (12)$$

and is done in a three steps approach.

First, a least-square algebraic fit of a plane into the circle's focus positions is performed followed by an orthogonal projection of the path y(s) onto the determined circular plane CP. On CP, a partial circle is fitted into the projected focus positions using a 2D algebraic least-square estimation method and then optimally represents the circle scan. Finally the line segment is determined perpendicular to the circular plane and connected to the end of the circle segment. The fitted trajectory can be described by the circular plane CP, the circle center $x_{center}$, the circle segment's radius R and the length and the position of the line segment.

It should be remembered that the position and the orientation of the volume coordinate system are given by the projection matrices $P_s$. A normalization of the coordinate system is performed. This is done by multiplying every $P_s$ from the right side with a transformation matrix $T_v \in \mathbb{R}^{4 \times 4}$ independent from s. The normalization consists of two operations, a translation $T_{v,t}$ to locate the origin at $x_{center}$ and a rotation $T_{v,r}$ that parallelizes the line direction with the $x_3$ axis. Thus $T_v = T_{v,r} \cdot T_{v,t}$. After the coordinate transform, the circular plane CP equals the $x_3 = 0$ plane and the trajectory is centered around the rotational axis with the line pointing in positive $x_3$ direction.

Further, the change of the relative position of the focus and the detector has to be handled. The detector coordinate system is adapted such that the fitted source trajectory is projected onto the detector on the same position as in the ideal case. Then, the filtering instructions of the known inversion algorithm can be applied without any further modification. Regarding the used C-arm hardware, it is sufficient to correct the in-plane translational movement of the pixel coordinate system, which is the most prominent deviation from the ideal geometry case. However, any other geometric deviation can be treated similarly. For every s, a translation matrix $T_{d,s} \in \mathbb{R}^{3 \times 3}$ is determined and multiplied to $P_s$ from the left, so that the volume coordinate origin always projects onto the same detector coordinates. By that, the coordinates of $\hat{C}$ become independent from the current misplacement of the detector area.

Finally, the modified projection matrices $$P_s^{mod} = T_{d,s} \cdot P_s \cdot T_v \quad (13)$$

describe the cone beam projection involving the normalized coordinate systems for the volume and for the detector. It should be noted that these projection matrices still represent the non-ideal acquisition geometry.

Experimental Results

The non-ideal acquisition geometry corresponding to a real world C-arm scan was evaluated in a study in order to validate the inventive adaption method. Further, the effects of the geometry deviations on the quality of the resulting images were noted.

The object of interest in this experiment was composed of mathematically defined geometric objects like ellipsoids or cubes and simulates the basic anatomical structure of a human head including homogeneous regions with embedded low contrast objects but also high contrast structures. Because of its composition, this so-called mathematical head phantom (see, for example, "http://www.imp.uni-erlangen.de/phantoms/head/head.html, head phantom description) is very demanding to the reconstruction approaches significantly revealing any type of artifact.

Two scans were simulated from the object, shifted by 4 cm along an axis. The first one involved ideal geometry and the second one included a series of projection matrices downloaded from a real world C-arm device and thus representing relevant geometry deviations. The reconstruction and simulation parameters are listed in Table 2.

Severe cone artifacts appeared in the FDK reconstructed images in contrast to the high quality image data resulting from the circle and line method. The simulated scans of ideal and non-ideal trajectories started at different angular positions. Thus, the orientation of artifacts differed. Involving non-ideal acquisition geometry, additional artifacts in both reconstruction approaches were detected. Some streak-like artifacts of low intensity appeared near the high contrast bone structure. The artifacts were due to some slight irregularities in angular sampling and to some remaining inexactness in the filtering step. In particular the matching of the contribution of the line and circular scan might be critical in more severe cases. Nevertheless, this experiment showed that the inventive adaptation is sufficient to consider geometrical distortions of real world C-arm devices.

TABLE 2

Reconstruction and Simulation Parameters

| | mathematical head | | |
|---|---|---|---|
| | voxelized head ideal geometry | ideal geometry | non-ideal geometry |
| detector dimension | 641 × 500 | 640 × 500 | 720 × 720 |
| pixel size | (0.6 mm)² | (0.6 mm)² | (0.580 mm)² |
| # projections on circle | 501 | 501 | 538 |

TABLE 2-continued

Reconstruction and Simulation Parameters

| | mathematical head | | |
|---|---|---|---|
| | voxelized head ideal geometry | ideal geometry | non-ideal geometry |
| # projections on each line | 221 | 196 | 196 |
| angular range of circle | 200 deg | 200 deg | 214 deg |
| length of each line | 220 mm | 195 mm | 195 mm |
| image volume dimension | 512 × 512 × 400 | 512 × 512 × 161 | 512 × 512 × 161 |
| voxel size | (0.422 mm)³ | 0.48 × 0.48 × 0.50 mm³ | 0.48 × 0.48 × 0.50 mm³ |

Although modifications and changes may be suggested by those skilled in the art, it is the intention of the inventor to embody within the patent warranted hereon all changes and modifications as reasonably and properly come within the scope of his contribution to the art.

We claim:

1. A method for reconstructing a CT image of a subject from data acquired from the subject, comprising the steps of:
    operating a C-arm x-ray apparatus, having a rotatable C-arm on which an x-ray source and a radiation detector are mounted, said x-ray source having a focus from which x-rays emanate in a cone beam, by rotating said focus around a subject through an actual focus trajectory consisting of an actual incomplete circle and an actual straight-line segment attached at an end of said actual incomplete circle, and detecting radiation emanating from said focus and attenuated by said subject, for each focus position in said actual focus trajectory, on said radiation detector;
    for each position of said focus in said actual focus trajectory, electronically calculating a projection matrix that, for that focus position, describes a perspective cone beam projection of the subject on the radiation detector;
    for use in a reconstruction algorithm based on a theoretical ideal trajectory consisting of an ideal incomplete circle and an ideal straight-line segment attached at an end of said ideal incomplete circle, adapting said theoretical ideal trajectory to said actual focus trajectory of said C-arm apparatus using said projection matrices to obtain an adapted ideal trajectory that is a best fit to said actual focus trajectory; and
    reconstructing an image of the subject using said reconstruction algorithm with said adapted ideal trajectory in place of said theoretical ideal trajectory in said reconstruction algorithm.

2. A method as claimed in claim 1 wherein said subject is composed of a plurality of voxels, and wherein said radiation detector is comprised of a plurality of detector image points, and comprising electronically calculating each projection matrix to define a relation between each voxel of said subject and coordinates of a corresponding detector image point.

3. A method as claimed in claim 1 comprising operating said C-arm apparatus to move said focus of said x-ray source through an actual focus trajectory consisting of an actual incomplete circle and one actual straight-line segment attached at one end of said actual incomplete circle, and employing an ideal trajectory in said reconstruction algorithm consisting of an ideal incomplete circle and one ideal straight-line segment attached at one end of said ideal incomplete circle.

4. A method as claimed in claim 1 comprising operating said C-arm apparatus to move said focus of said x-ray source through an actual focus trajectory consisting of an actual incomplete circle having opposite ends, and two actual straight-line segments respectively attached at said two ends of said incomplete circle, said two actual straight-line segments being disposed at a same side of said actual incomplete circle, and employing an ideal trajectory in said reconstruction algorithm consisting of an ideal incomplete circle having opposite ends and two ideal straight-line segments respectively attached at said ends of said incomplete circle, said two ideal straight-line segments being disposed at a same side of said ideal incomplete circle.

5. A method as claimed in claim 1 comprising operating said C-arm apparatus to move said focus of said x-ray source through an actual focus trajectory consisting of an actual incomplete circle having opposite ends, and two actual straight-line segments respectively attached at said two ends of said incomplete circle, said two actual straight-line segments being disposed at opposite sides of said actual incomplete circle, and employing an ideal trajectory in said reconstruction algorithm consisting of an ideal incomplete circle having opposite ends and two ideal straight-line segments respectively attached at said ends of said incomplete circle, said two ideal straight-line segments being disposed at opposite sides of said ideal incomplete circle.

6. A method as claimed in claim 1 comprising adapting said theoretical ideal trajectory to said actual trajectory, to obtain said adapted ideal trajectory, using a cost function.

7. A method as claimed in claim 6 comprising adapting said theoretical ideal trajectory to said actual trajectory, to obtain said adapted ideal trajectory, by automatically electronically finding a least-squares fit of said ideal trajectory to said actual trajectory.

* * * * *